United States Patent [19]

Arlt

[11] Patent Number: 5,449,811
[45] Date of Patent: Sep. 12, 1995

[54] PROCESS FOR THE PRODUCTION OF 1-AMINO-1-METHYL-3(4)-CYANOCYCLOHEXANE

[75] Inventor: Dieter Arlt, Köln, Germany

[73] Assignee: Bayer Aktiengesellschaft, Leverkusen, Germany

[21] Appl. No.: 372,534

[22] Filed: Jan. 13, 1995

[30] Foreign Application Priority Data

Jan. 24, 1994 [DE] Germany ................. 44 01 929.7

[51] Int. Cl.$^6$ ............... C07C 253/30; C07C 253/10; C07C 255/46
[52] U.S. Cl. ............................ 558/431; 558/335
[58] Field of Search ................... 558/431, 335

[56] References Cited

U.S. PATENT DOCUMENTS

| 4,613,685 | 9/1986 | Klein et al. | 560/330 |
| 4,835,239 | 5/1989 | Klein et al. | 528/44 |

FOREIGN PATENT DOCUMENTS 1965004  7/1971  Germany.

OTHER PUBLICATIONS

Weygand/Hilgetag, "Preparative Organic Chemistry", (1972), p. 351; John Wiley & Sons–N.Y., London, Sydney.

*Primary Examiner*—Joseph Paul Brust
*Attorney, Agent, or Firm*—Joseph C. Gil; Lyndanne M. Whalen

[57] ABSTRACT

A new process for the production of 1-amino-1-methyl-3(4)-cyanocyclohexane (AMCC), an intermediate for the manufacture of 1-isocyanato-1-methyl-3(4)-isocyanatomethylcyclohexane. In this process, 4(5)-cyano-1-methylcyclohexene is reacted with excess hydrogen cyanide in the presence of aqueous sulfuric acid to form 1-formamido-1-methyl-3(4)-cyanocyclohexane which is then selectively hydrolyzed in an acidic medium to form AMCC.

26 Claims, No Drawings

PROCESS FOR THE PRODUCTION OF 1-AMINO-1-METHYL-3(4)-CYANOCYCLOHEXANE

BACKGROUND OF THE INVENTION

The present invention relates to a new process for the manufacture of 1-amino-1-methyl-3(4)-cyanocyclohexane (AMCC), which can be converted by hydrogenation to 1-amino-1-methyl-3(4)-amino-methyl-cyclohexane (AMCA), the intermediate for the manufacture of 1-isocyanato-1-methyl-3(4)-isocyanatomethyl-cyclohexane (IMCI).

EP-A 0 153 561 discloses that IMCI is a diisocyanate of high quality that has a variety of uses in polyurethane chemistry. IMCI may be obtained by the following schematic synthesis sequence:

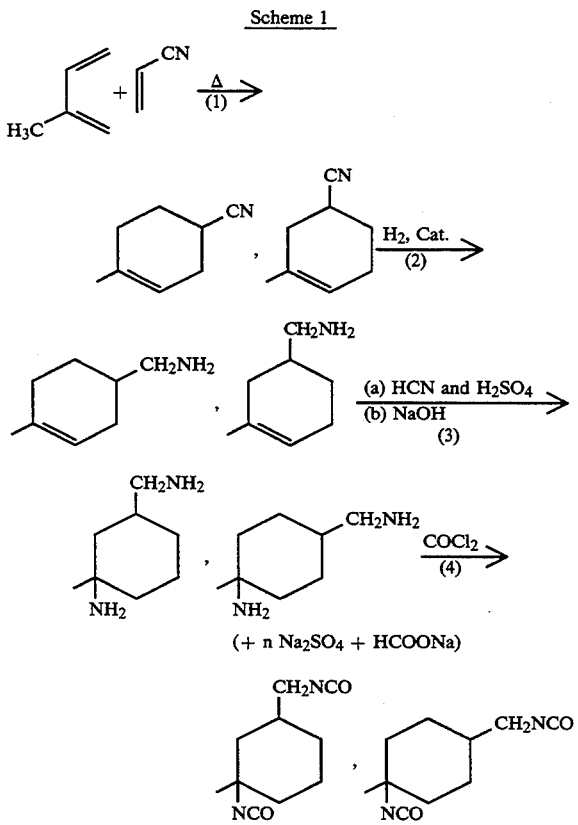

A key step in the course of this reaction scheme is the Ritter reaction (3). This reaction makes it possible to introduce an amino group bonded to a tertiary carbon atom. The Ritter reaction is preferably carried out in sulfuric acid because the corresponding formamide is primarily formed from the olefinic intermediate and hydrogen cyanide and subsequently hydrolyzed. The salt of AMCA, which is present in solution in the reaction mixture, is formed in this way. As is customary in the workup of Ritter reaction mixtures, the diamine is subsequently liberated with alkaline materials (e.g. caustic soda solution) and isolated by extraction with suitable solvents from the aqueous solution of the alkali metal salts.

In the course of the synthesis in accordance with the above-illustrated scheme, a large amount of unusable waste salts is formed. This waste makes large-scale production by this process prohibitive due to the environmental pollution generated. A stoichiometric consideration of Examples (1a) and (1b) of EP-A-0 153 561 shows that in the best case more than 4 t of a waste mixture of sodium sulfate and formate is formed. In the least favorable case, nearly 9 t of this waste are generated per metric ton of AMCA.

SUMMARY OF THE INVENTION

It is an object of the present invention to provide a process for the production of AMCC from 4(5)-cyano-1-methylcyclohexene (CMC) without generating waste salts.

It is another object of the present invention to provide a process in which IMCI is ultimately obtained from isoprene and acrylonitrile in which substantially no waste salts are generated.

These and other objects which will be apparent to those skilled in the art are accomplished by reacting 4(5)-cyano-1-methylcyclohexene (CMC) with hydrogen cyanide in the presence of sulfuric acid to form 1-formamido-1-methyl-3(4)-cycanocyclohexane (FMCC) and then selectively hydrolyzing the FMCC to form AMCC. Here and in the following "4(5)" and "3(4)" shall mean that mixtures of the 4- and 5-isomers resp. of the 3- and 4-isomers are meant.

DETAILED DESCRIPTION OF THE PRESENT INVENTION

The reaction scheme for the process of the present invention is as follows:

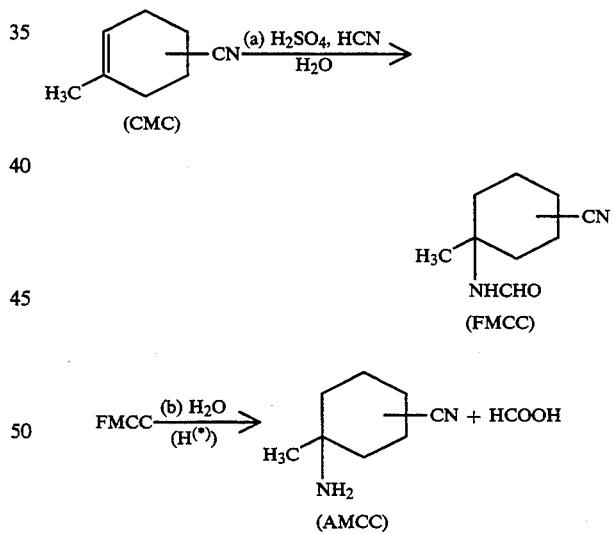

The present invention provides a process for the production of 1-amino-1-methyl-3(4)-cyanocyclohexane (AMCC) in which 4(5)-cyano-1-methylcyclohexene (CMC) is first converted to 1-formamido-1-methyl-3(4)-cyanocyclohexane (FMCC) with an excess of hydrogen cyanide in the presence of aqueous, but at least 50 wt %, sulfuric acid in an amount of at least 1 mole of $H_2SO_4$ per mole of CMC. The reaction mixture, optionally with preceding and/or simultaneous addition of water, is subsequently distilled to remove excess hydrogen cyanide. The FMCC thus formed, is then selectively hydrolyzed in aqueous acidic medium to form AMCC.

The CMC used as starting material is known and may be readily prepared from isoprene and acrylonitrile by a cycloaddition reaction.

The first step of the process of the present invention is the reaction of CMC with hydrogen cyanide in hydrous sulfuric acid. This reaction is carried out in 50 to about 96 wt % sulfuric acid, and at least the stoichiometrically necessary amount of water, based on the amount of CMC. The molar ratio of hydrogen cyanide to CMC is generally from about 2:1 to about 20:1, preferably from about 8:1 to about 20:1. At least 1 mole of $H_2SO_4$ is present in the reaction mixture for each mole of CMC. The molar ratio of $H_2SO_4$ to CMC is preferably from about 1.5:1 to about 3:1. The reaction is generally conducted at a temperature of from about 0° to about 100° C. and at a pressure of from about 1 to about 10 bar. The reaction time for the conversion depends both on the chosen reaction temperature and on the sulfuric acid and hydrogen cyanide concentrations. Suitable reaction times are generally in the range of from a few minutes to hours.

In general, the CMC is added to a mixture of sulfuric acid and hydrogen cyanide. Care should be taken to ensure thorough mixing, e.g. by stirring, of the reaction mixture. The reaction may be carried out either discontinuously (e.g., in an agitated tank) or continuously (e.g., in a series of stirred-tank reactors or in a tubular reactor). The exothermic heat of reaction may be dissipated by appropriate cooling arrangements such as reflux cooling of the boiling hydrogen cyanide. In one embodiment, this reaction of CMC with hydrogen cyanide is carried out adiabatically and the heat of reaction is used for the subsequent vaporization of excess hydrogen cyanide. This reaction is in principle described in German Offenlegungsschrift 1,965, 004.

Upon completion of the reaction of CMC with hydrogen cyanide, the hydrogen cyanide present in excess is separated from the reaction mixture by distillation. Water may be added prior to or during this distillation. The addition of water is advantageous where the aqueous-acidic reaction mixture in dilute form is to be further treated and returned to the vessel in which a subsequent reaction of CMC and hydrogen cyanide is to be conducted.

The FMCC present in the reaction mixture remaining after this distillation is then selectively hydrolyzed to AMCC in an aqueous acidic medium using any one of several techniques.

The fact that this selective hydrolysis splits off the formyl group to produce AMCC in good yield is considered surprising because those skilled in the art expect (See, e.g., C. Ferri, *Reaktionen d. orq. Synthese*, Georg Thieme Verlag Stuttgart 1978, p. 202 and literature quoted therein) nitriles to be hydrolyzed in an acidic medium to produce carboxylic acids or carboxylic acid amides. It would therefore be expected that hydrolysis of the formamidonitrile would produce the corresponding aminocarboxylic acid or its amide as the reaction product.

The selective hydrolysis of the present invention may be carried out in a variety of ways. However, each method for the selective hydrolysis of FMCC is generally conducted in an aqueous acidic reaction medium at a temperature of from about 40° to about 150° C., optionally with appropriate application of pressure. It is preferred that sulfuric acid be used but formic acid or an acidified ion exchanger or combinations of sulfuric acid, formic acid and acidified ion exchanger may be used as the acid. The acid concentration of the aqueous acidic reaction medium in which selective hydrolysis is carried out can vary within wide ranges. Suitable acid concentrations range from about 0.5 to about 65 wt %, preferably from about 0.5 to about 50 wt % aqueous acid. The acid is generally used in an amount of from about 1 to about 200 mole %, based on the amount of FMCC present.

In one embodiment of the present invention, the selective hydrolysis is conducted directly after removal of the excess hydrogen cyanide by distillation without intermediate isolation of the FMCC. In this embodiment, the sulfuric acid reaction solution may be further diluted to an acid concentration, based on the sulfuric acid and water present in the reaction mixture (without inclusion of other constituents), of up to 65 wt %, preferably from about 0.5 to about 50 wt % before hydrolysis at a temperature within the 40° to 150° C. temperature range and an acid concentration of up to about 65 wt %. During the selective hydrolysis, the formyl group present in the FMCC is split off. The acid present in the reaction mixture is neutralized with ammonia, preferably aqueous ammonia, and the AMCC is subsequently isolated by extraction with suitable solvents.

Solvents suitable for this extraction include: chlorinated hydrocarbons such as dichloromethane and chlorobenzene; ethers such as tert-butyl methyl ether; esters such as ethyl and n-butyl acetate; ketones such as methyl ethyl ketone and cyclohexanone; alcohols such as n- and isobutanol, 1-pentanol, 2-methyl-1-butanol and 2-ethylhexanol; and mixtures of such solvents.

After the extraction, solvent may be separated from the organic phase by vacuum distillation and reused. If desired, the crude AMCC can be freed from minor impurities by distillation. It is also possible, however, to hydrogenate the crude AMCC reaction product to form AMCA or to use the organic phase remaining after the aforementioned extraction directly (i.e., without distilling off the solvent), provided the solvent used for the extraction is suitable both for the extraction and for the subsequent use (e.g., hydrogenation). The solvent may be separated from the organic phase which still contains solvent after use (e.g., hydrogenation) and recovery of the product (e.g., AMCA). The separated solvent may be used in subsequent extractions. This ability to reuse solvent minimizes the expense of workup and the consumption of solvent.

The aqueous acidic phase generated during the above-described extraction can also be worked up and reused.

In a second embodiment of the present invention, additional water may optionally be added to the reaction mixture containing FMCC which has been freed from excess hydrogen cyanide. This additional water may be added in an amount such that the sulfuric acid component of the mixture is from about 20 to about 70 wt %. The FMCC is then extracted from this aqueous acidic reaction mixture with solvents of the same type described above with respect to the first embodiment. The FMCC is then recovered from the solvent phase by distillation to remove the solvent. This crude FMCC product may be used directly or after distillative isolation (e.g., vacuum distillation) in the subsequent selective hydrolysis. The nature and concentration of the acids added and the reaction temperature(s) used in this selective hydrolysis correspond to those described above in greater detail with respect to the first embodiment of this invention.

During the hydrolysis of the FMCC to AMCC, an equivalent amount of formic acid is formed. Therefore, the aqueous phase always remains acidic. For this reason, only a catalytically effective amount of sulfuric acid should be used for the hydrolysis. When only the catalytically effective amount of sulfuric acid is used, the aqueous phase remaining after neutralization with ammonia and solvent extraction of the AMCC formed principally contains ammonium formate salt which may optionally be isolated.

In this second embodiment of the process of the present invention, a small portion of the aqueous phase obtained after the first extraction may be removed prior to neutralization and used as the catalyst for the selective hydrolysis. An amount of (fresh) sulfuric acid corresponding to the amount of aqueous phase used as catalyst in the hydrolysis is included at the beginning of the process of the present invention (i.e., the reaction mixture of CMC and hydrogen cyanide) during a subsequent reaction cycle. In this way, an undesirable accumulation of by-products in the reaction medium can be avoided.

In the second embodiment of the process of the present invention, the sulfuric acid used in the first stage is not neutralized and only catalytic amounts of sulfuric acid need be used in the selective hydrolysis. The amount of salts generated is minimized. The relatively small amount of acid to be neutralized makes it possible to neutralize that acid using alkaline neutralization agents, such as caustic soda solution, if the relatively small amounts of alkali metal salts generated are acceptable.

To isolate the AMCC product, the aqueous acidic reaction mixture present after the hydrolysis is neutralized with ammonia and the AMCC is extracted with a solvent of the type previously described. The organic phase containing the AMCC may be worked up or subsequently used in the same manner as was described above with respect to the first embodiment of the present invention.

The aqueous phase present after the extraction can optionally be worked up for the manufacture of ammonium formate or in the same manner described more fully below with respect to the third embodiment of this invention.

In a third embodiment of the process of the present invention, the aqueous acidic reaction mixture which has been freed from excess hydrogen cyanide and optionally diluted with water, is neutralized with ammonia and a further quantity of water may optionally be added in an amount such that the mixture has a content of ammonium salts of from about 20 to about 70 wt %. The FMCC present in the mixture is subsequently extracted with solvent and further processed in the same manner described above with respect to the second embodiment of the process of the present invention.

In this embodiment of the process of the present invention, the entire amount of sulfuric acid used in the initial reaction is neutralized. A considerable amount of ammonium salts requiring workup is therefore formed. This embodiment is a preferred procedure because the extraction is substantially complete, even when the solution is relatively concentrated. As a result, the energy expended for the workup is reduced.

All extractions may be carried out by any of the conventional techniques in any of the conventional devices. For example, the extraction may be carried in mixing and separating vessels, preferably on a continuous basis (e.g., in cascades with mixing and separating vessels coupled in series), or in extraction columns.

It is particularly surprising that AMCC which has a higher basicity than ammonia can be extracted in good yields from the ammonia solutions formed by neutralization with ammonia. This extractability, in addition to the unexpected selective hydrolysis of the FMCC, is, however, essential if the process of the present invention is to be commercially viable.

If the aqueous phases generated in the individual extractions are salt solutions, they can obviously be worked up to recover the salts dissolved therein. Preferably, however, the workup of the individual aqueous phases is carried out, separately or together, to recover concentrated sulfuric acid which can be reused at the start of the process or sulfur dioxide which is suitable for the manufacture of sulfuric acid. Workup of dilute sulfuric acid solutions may simply be concentration of the solution to the desired concentration level. Aqueous ammonium sulfate and/or ammonium formate solutions, possibly containing excess sulfuric acid may be thermally decomposed in accordance with known techniques to liberate nitrogen, water, possibly carbon dioxide and sulfur dioxide. This thermal decomposition generally occurs at temperatures of $>1000°$ C.

The AMCC obtained in accordance with any of the embodiments of the process according to the invention may be hydrogenated by any of the known techniques to form AMCA which may be converted to IMCI by phosgenation in accordance with known techniques.

Having thus described my invention, the following Examples are given as being illustrative thereof. In these Examples, all percentages are based on weight.

EXAMPLES

Example 1

363 g (3 moles) of 4(5)-cyano-1-methyl-cyclohexene(CMC) (an isomer mixture obtained by cycloaddition of isoprene and acrylonitrile) were steadily charged to a mixture of 108 g of water, 600 g of 96% sulfuric acid and 900 ml of hydrogen cyanide at a temperature of from 27° to 29° C. by means of a metering pump with stirring over a period of 1.5 hours. The heat of reaction was dissipated by reflux cooling of the boiling hydrogen cyanide. 10 minutes after addition of the CMC had been completed, 546 g water were added and the excess hydrogen cyanide was simultaneously distilled off, initially at normal pressure and towards the end, at reduced pressure. When the reaction mixture was at 20° to 30° C., 816 g of 25% aqueous $NH_3$ solution were charged to the mixture while the mixture was stirred and cooled with ice water. The ammoniated reaction solution was subsequently extracted with 1000 ml of dichloromethane three times. After removal of the solvent in a rotary evaporator, 521.5 g of crude 1-formamido-1-methyl-3(4)-cyanocyclohexane isomer mixture were obtained The product had a purity of 90% (as determined by Gas Chromatography). 469 g of pure product (94.2% of the theoretical amount) were recovered.

Example 2 (First Embodiment)

363 g (3 moles) of 4(5)-cyano-1-methyl-cyclohexene were steadily charged to a reaction vessel containing a mixture of 108 g of water, 600 g of 96% sulfuric acid and 1200 ml of hydrogen cyanide at a temperature of from 27° to 29° C. over a period of 90 minutes by means of a metering pump while stirring the mixture. The heat of reaction was dissipated by reflux cooling of the boiling hydrogen cyanide. 10 minutes after the addition of CMC was completed, 792 g of water were added and the excess hydrogen cyanide simultaneously distilled off. The reaction mixture was subsequently heated for 300 minutes at 60° C. and then, while cooling to 20° to 30° C., ammoniated by adding 1100 g of 25% aqueous $NH_3$ solution. The mixture was subsequently extracted with 1000 ml of dichloromethane three times. After removal of the solvent in a rotary evaporator, 380 g of crude product were obtained. After distillation in a thin-film evaporator, 350 g (84% of the theoretical amount) of pure 1-amino-1-methyl-3(4)-cyanocyclohexane (isomer mixture) were recovered.

Example 3

5.0 g of 1-formamido-1-methyl-3(4)-cyanocyclohexane were dissolved with stirring in 12 g of 48% sulfuric acid. The mixture was heated at 80° C. for 165 minutes and 27 ml of aqueous ammonia solution (25% $NH_3$ content) were then added while cooling to 20° C. The aqueous phase was subsequently extracted with 25 ml of dichloromethane three times. After evaporation to low bulk on a rotary evaporator, 3.0 g (72.2% of the theoretical amount) of a pure mixture of isomers of 1-amino-1-methyl-3(4)-cyanocyclohexane were obtained.

Example 4

44.9 g of 1-formamido-1-methyl-3(4)-cyanocyclohexane were charged with stirring into 120 g of 48% sulfuric acid. The mixture was then heated for 90 minutes at 80° C., subsequently ammoniated by adding 110 g of 25% $NH_3$ solution and then extracted with 250 ml of dichloromethane twice. After evaporation to low bulk on a rotary evaporator, 30.7 g of isomeric 1-amino-1-methyl-3(4)-cyanocyclohexanes were obtained. According to GC analysis, the product mixture still contained 1.9% of unreacted material. 80.6% of the theoretical yield of the desired aminonitriles was obtained.

Example 5

432 g of 1-formamido-1-methyl-3(4)-cyanocyclohexane were charged with stirring into 1500 g of 38.4% sulfuric acid. The mixture was then heated for 5 hours 35 minutes at 60° C. The solution was subsequently ammoniated at 20° C. by adding 1100 g of 25% $NH_3$ solution. The reaction product was extracted from the water phase with 1000 ml of dichloromethane three times. After evaporation to low bulk on a rotary evaporator, 357 g (99.4% of the theoretical amount) of a mixture of isomeric 1-amino-1-methyl-3(4)-cyanocyclohexanes were obtained.

Example 6

A mixture of 25 g of 1-formamido-1-methyl-3(4)-cyanocyclohexane and 100 ml of 1% aqueous sulfuric acid was heated at 100° C. for 74 hours with stirring. The reaction mixture was then evaporated to low bulk in the vacuum rotary evaporator. The concentrate obtained (37.6 g) was ammoniated by adding 12 ml of 25% aqueous ammonia solution and subsequently extracted with 50 ml of dichloromethane three times. After reduction of the organic phase to low bulk in a rotary evaporator, 19.9 g of a mixture that according to GC analysis contained 71.3% of 1-amino-1-methyl-3(4)-cyanocyclohexane and 27.8% of 1-formamido-1-methyl-3(4)-cyanocyclohexane was obtained. The product mixture could be split up by fractional distillation in vacuum and the remaining fraction recycled to a mixture to be subjected to hydrolysis.

Example 7

A mixture of 50 g of 1-formamido-1-methyl-3(4)-cyanocyclohexane, 200 g of water and 5 g of acidic ion exchanger (commercially available under the name Dowex 50 WX 8) was heated with stirring for 90 hours at 100° C. The ion exchanger was subsequently filtered off and the flitrate concentrated in a vacuum rotary evaporator. 50 ml of 25% aqueous $NH_3$ solution were added to the concentrate which was then extracted with 150 ml of dichloromethane three times. After reduction of the organic phase to low bulk, 42 g of a mixture made up of 64.8% AMCC and 25.2% FMCC were obtained. The reaction had proceeded with a selectivity of 100%. The aqueous phase contained ammonium formate exclusively.

Example 8 (Second Embodiment)

(a) 363 g (3 moles) of 4(5)-cyano-1-methylcyclohexene (isomer mixture obtained by cycloaddition of isoprene and acrylonitrile) were steadily added to a mixture of 108 g of water, 600 g of 96% sulfuric acid and 900 ml of hydrogen cyanide at a temperature of 27° to 29° C. over a period of 1.5 hours by means of a metering pump with stirring. The heat of reaction was dissipated by reflux cooling of the boiling hydrogen cyanide. 10 minutes after the addition of the isomer mixture was completed, 546 g of water were added and the excess hydrogen cyanide subsequently distilled off in vacuum. The temperature of the reaction mixture was maintained at 30° C. The reaction mixture was then further diluted by adding 800 g of water and subsequently extracted with 1 l of dichloromethane three times.

After removal of the dichloromethane in a rotary evaporator, 471 g of crude 1-formamido-1-methyl-3(4)-cyanocyclohexane isomer mixture (93.8% purity as determined by GC analysis) was obtained.

The aqueous phase was concentrated in vacuum in a thin film evaporator at a wall temperature of 50° C. 762 g of concentrate were obtained. 76 g of this concentrate were taken and fed to a thermal decomposition for the recovery of $SO_2$.

The residual amount of the concentrate was then supplemented with 76 g of fresh 80% sulfuric acid and re-used as the acidic reaction phase in the first stage of the process of the present invention. After addition of 900 ml of hydrogen cyanide, 302.5 g of CMC were reacted under the same conditions as were used above. After the working up the reaction mixture in the same manner and under the same conditions described above, 388 g of crude 1-formamido-1-methyl-3(4)-cyanocyclohexane isomer mixture were obtained. (b) 471 g of the 1-formamido-1-methyl-3(4)-cyanocyclohexane isomer mixture obtained above in (a) were mixed with 76 g of the sulfuric acid concentrate obtained in (a) and 250 g of water and heated for 30 hours at 100° C. The solution was then neutralized by adding 85 g of 25% aqueous ammonia solution and then concentrated by distilling off water in a vacuum rotary evaporator. The solid obtained was dissolved in 353 g of 21% aqueous ammonia solution and subsequently extracted with 1000 ml of dichloromethane three times. After distilling off the extractant, 361 g of crude AMCC of 94% purity (determined by gas chromatography) or 87% of the theoretical amount were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of 1-amino-1-methyl-3(4)-cyanocyclohexane comprising
    a) reacting
        (1) 4(5)-cyano-1-methylcyclohexene with
        (2) excess hydrogen cyanide in the presence of
        (3) aqueous sulfuric acid which is at least 50 wt % sulfuric acid in an amount such that at least 1 mole of sulfuric acid is present for each mole of 4(5)-cyano-1-methylcyclohexene to form 1-formamido-1-methyl-3(4)-cyanocyclo-hexane,
    b) distilling off excess hydrogen cyanide,
    c) selectively hydrolyzing the 1-formamido-1-methyl-3(4)-cyanocyclohexane formed in a) in an aqueous acidic medium to form 1-amino-1-methyl-3(4)-cyanocyclohexane.

2. The process of claim 1 in which water is added to the reaction mixture from a) prior to step b).

3. The process of claim 1 in which water is added to the reaction mixture from a) during step b).

4. The process of claim 1 in which water is added to the reaction mixture remaining after step b).

5. The process of claim 1 in which water is added to the reaction mixture from step a) before, during and/or after step b) in an amount such that the sulfuric acid content of the mixture, based on sulfuric acid and water alone, is up to 65% by weight.

6. The process of claim 5 in which step c) is carried at a temperature of from about 40° to 150° C.

7. The process of claim 6 in which sulfuric acid present upon completion of step c) is neutralized with ammonia.

8. The process of claim 7 in which the product 1-amino-1-methyl-3(4)-cyanocyclohexane is recovered by solvent extraction.

9. The process of claim 1 in which the reaction mixture remaining after step b)is subjected to solvent extraction to isolate 1-formamido-1-methyl-3(4)-cyanocyclohexane and the isolated 1-formamido-1-methyl-3(4)-cyanocyclohexane is subjected to step c).

10. The process of claim 9 in which water is added to the reaction mixture prior to solvent extraction.

11. The process of claim 1 in which any sulfuric acid present in the reaction mixture remaining after step b) is neutralized by adding ammonia.

12. The process of claim 11 in which the 1-formamido-1-methyl-3(4)-cyanocyclohexane present in the neutralized mixture is isolated by solvent extraction and subsequently subjected to step c).

13. The process of claim 1 in which the aqueous acid used in step c) is a 0.5 to 65 wt % aqueous formic acid or sulfuric acid solution.

14. The process of claim 13 in which the total amount of aqueous acid is from about 1 to about 200 mole %, based on the amount of 1-formamido-1-methyl-3(4)-cyanocyclohexane present.

15. The process of claim 14 in which step c) is carried out at a temperature of from about 40° to about 150° C.

16. The process of claim 14 in which step c) is carried out under pressure.

17. The process of claim 14 in which any acid remaining upon completion of step c) in neutralized by adding ammonia.

18. The process of claim 14 in which the 1-amino-1-methyl-(3(4)-cyanocyclohexane is isolated by solvent extraction.

19. The process of claim 1 in which step c) is carried out in the presence of an acidic ion exchanger.

20. The process of claim 1 in which 1-formamido-1-methyl-3(4)-cyanocyclohexane is isolated from the reaction mixture remaining after step b) by solvent extraction and/or the 1-amino-1-methyl-3(4)-cyanocyclohexane remaining after step c) is isolated by solvent extraction.

21. The process of claim 20 in which the phase or phases containing sulfuric acid or ammonium sulfate or ammonium formate which remain after solvent extraction are concentrated to produce sulfuric acid which is reusable in step a).

22. The process of claim 20 in which the phase or phases containing sulfuric acid or ammonium sulfate or ammonium formate which remain after solvent extraction are subjected to thermolytic decomposition to split off sulfur dioxide which can be used to produce sulfuric acid.

23. A process for the production of 1-amino-1-methyl-3(4)-cyanocyclohexane comprising hydrolyzing 1-formamido-1-methyl-3(4)-cyanocyclohexane in an aqueous acidic phase at 40° to 150° C. to form 1-amino-1-methyl-3(4)-cyanocyclohexane.

24. The process of claim 23 in which acid present in the mixture remaining upon completion of the hydrolysis is neutralized by adding ammonia.

25. The process of claim 24 in which the 1-amino-1-methyl-3(4)-cyanocyclohexane is recovered from the neutralized mixture by extraction with an organic solvent.

26. The process of claim 23 in which the hydrolysis is carried out in the presence of a 0.5 to 50 wt % aqueous sulfuric acid.

* * * * *